(12) United States Patent
Sasaki

(10) Patent No.: US 10,586,948 B2
(45) Date of Patent: Mar. 10, 2020

(54) ORGANIC ELECTRO-LUMINESCENT DISPLAY DEVICE INCLUDING MOISTURE DETECTION MEMBER

(71) Applicant: Japan Display Inc., Minato-ku (JP)

(72) Inventor: Yusuke Sasaki, Minato-ku (JP)

(73) Assignee: Japan Display Inc., Minato-ku (JP)

( * ) Notice: Subject to any disclaimer, the term of this patent is extended or adjusted under 35 U.S.C. 154(b) by 0 days.

(21) Appl. No.: 15/904,932

(22) Filed: Feb. 26, 2018

(65) Prior Publication Data

US 2018/0254435 A1  Sep. 6, 2018

(30) Foreign Application Priority Data

Mar. 1, 2017 (JP) ................. 2017-037946

(51) Int. Cl.
*H01L 51/00* (2006.01)
*H01L 51/52* (2006.01)
*G01N 31/22* (2006.01)

(52) U.S. Cl.
CPC ....... *H01L 51/5253* (2013.01); *G01N 31/222* (2013.01); *H01L 51/0031* (2013.01); *H01L 51/5259* (2013.01); *G01N 31/221* (2013.01)

(58) Field of Classification Search
CPC . H01L 51/5253; G01N 31/221; G01N 31/222

USPC ........................................ 257/40; 438/82, 99
See application file for complete search history.

(56) References Cited

U.S. PATENT DOCUMENTS

2010/0295759 A1* 11/2010 Tanaka ................ H01L 51/5256
345/76
2016/0372528 A1* 12/2016 Kamura .............. H01L 51/0096

FOREIGN PATENT DOCUMENTS

JP         2010-272270        12/2010

* cited by examiner

*Primary Examiner* — Didarul A Mazumder
(74) *Attorney, Agent, or Firm* — Oblon, McClelland, Maier & Neustadt, L.L.P.

(57) ABSTRACT

An organic electro-luminescent display device according to an embodiment of the present invention includes a thin film transistor substrate including a base member; an organic material layer disposed on the base member in a display area and held between a lower electrode and an upper electrode; a dam formed on the base member in an external area surrounding the display area; and a sealing layer formed on the organic material layer, the sealing layer covering the display area, the sealing layer including a sealing planarization film formed of organic material and formed in an area surrounded by the dam, the sealing layer further including a sealing film formed of inorganic material and covering the dam. The dam includes moisture detection member.

7 Claims, 3 Drawing Sheets

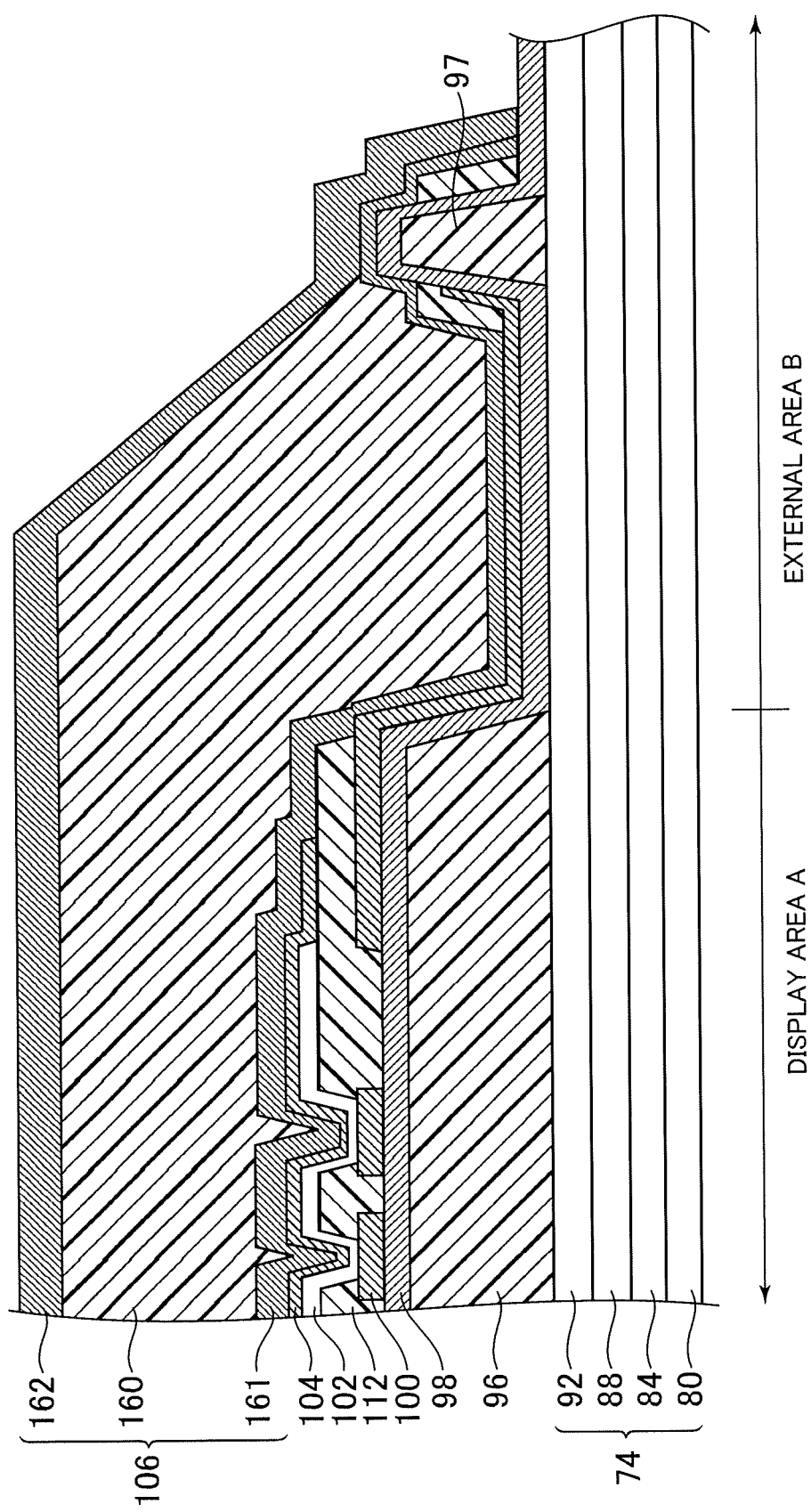

ORGANIC ELECTRO-LUMINESCENT DISPLAY DEVICE INCLUDING MOISTURE DETECTION MEMBER

CROSS-REFERENCE TO RELATED APPLICATION

The present application claims priority from Japanese Application JP2017-37946 filed on Mar. 1, 2017, the content of which is hereby incorporated by reference into this application.

BACKGROUND OF THE INVENTION

1. Field of the Invention

The present invention relates to organic electro-luminescent (EL) display devices.

2. Description of the Related Art

An organic EL display device includes a display panel having a thin film transistor (TFT) and an organic light emitting diode (OLED) formed on a base member.

In the above organic EL display device, a display area including light emitting elements is sealed whereby the light emitting elements are protected against moisture or the like, for example, as is disclosed in Japanese Patent Laid-open Publication No. 2010-272270.

SUMMARY OF THE INVENTION

The sealing is achieved, for example, by a method using a combination of an inorganic material film and an organic material film. If there is a defect in the sealed area, for example, moisture will enter the organic material film and reach the light emitting elements. Such moisture can cause failure in light emission.

To address the above problem, it is an object of one or more embodiments of the present invention to early detect a possibility of such a failure in light emission.

An organic EL display device according to an embodiment of the present invention includes a thin film transistor substrate including a base member; an organic material layer disposed on the base member in a display area and held between a lower electrode and an upper electrode; a dam formed on the base member in an external area surrounding the display area; and a sealing layer formed on the organic material layer, the sealing layer covering the display area, the sealing layer including a sealing planarization film formed of organic material and formed in an area surrounded by the dam, the sealing layer further including a sealing film formed of inorganic material and covering the dam. The dam includes moisture detection member.

BRIEF DESCRIPTION OF THE DRAWINGS

FIG. 3 is a cross sectional view of the organic EL display device illustrated in FIG. 1 along the line III-III.

DETAILED DESCRIPTION OF THE INVENTION

Figure 1:
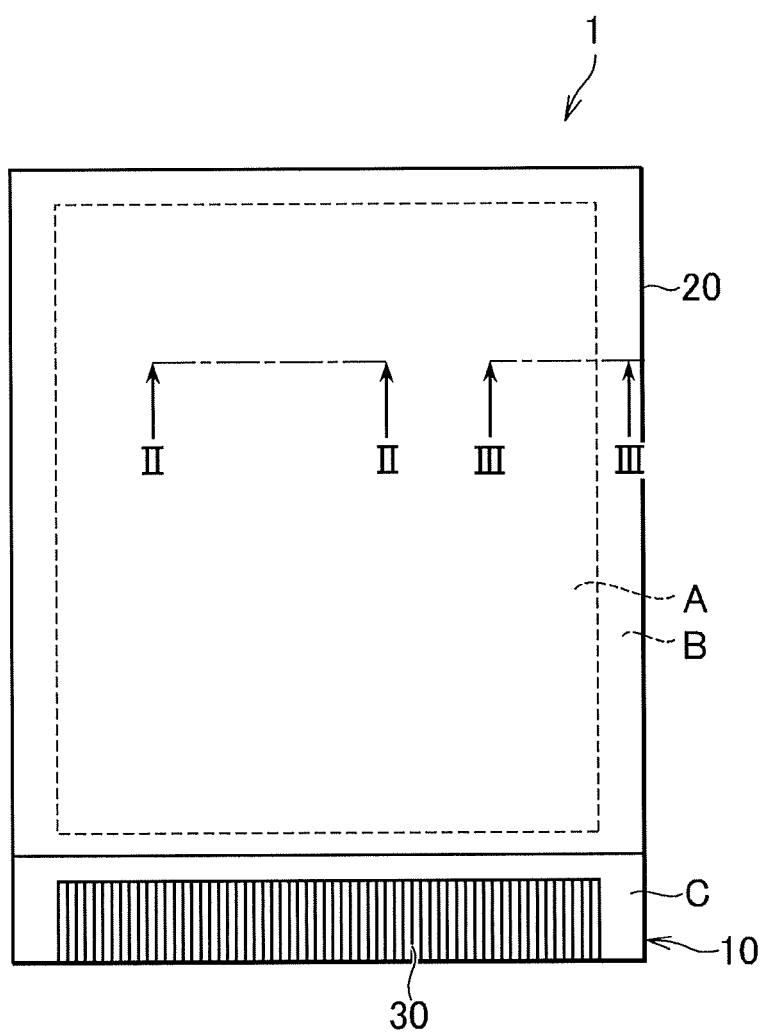
FIG. 1 is a schematic plan view of an organic EL display device according to an embodiment of the present invention.

The following describes an embodiment of the present invention, with reference to the drawings. The disclosure, however, is mere one example, and modification of the present invention that can be readily achieved by a person skilled in the art without departing from the gist of the present invention is included in the scope of the present invention. The drawings are given only for purpose of clear explanation of the present invention. The widths, thicknesses, and shapes of respective units may be illustrated schematically in the drawings, compared with actual dimensions and shapes. These, however, are only examples, and should not limit the interpretation of the present invention in any way. In the specification and drawings, an element mentioned earlier is given the same reference numbers, and may not be repetitively described in detail.

FIG. 1 illustrates a schematic structure of an organic electro-luminescent (EL) display device according to an embodiment of the present invention. The organic EL display device 1 includes a thin film transistor substrate 10 and a counter substrate 20 opposed to a part of the thin film transistor substrate 10. As illustrated in FIG. 1, the thin film transistor substrate 10 has a display area A that displays an image, an external area B surrounding the display area, and a component mount area C.

The display area A is a substantially rectangular area on which organic light emitting diodes (OLED) (not shown) corresponding to respective pixels are disposed in a matrix. The external area B is a frame area surrounding the substantially rectangular display area A. Specific structures of the display area A and the external area B will be described later.

The component mount area C is a partial area of the thin film transistor substrate 10, the area having no counter substrate 20 opposed to the area. The component mount area C has an external connection terminal 30. The component mount area C may additionally have a driver IC and other components. The external connection terminal 30 is a terminal for electrical connection to an external device and is electrically connected to an external device, for example, via a flexible printed circuit board (FPC). The external connection terminal 30 receives image data from an external device and supplies a voltage signal to be applied to the respective pixels to the OLEDs via a driver IC (not shown). The component mount area C, which is defined along one side of the thin film transistor substrate 10 in FIG. 1, may be defined along two or more sides of the thin film transistor substrate 10.

The following describes a specific structure of the display area A and the external area B of the thin film transistor substrate 10.

Figure 2:
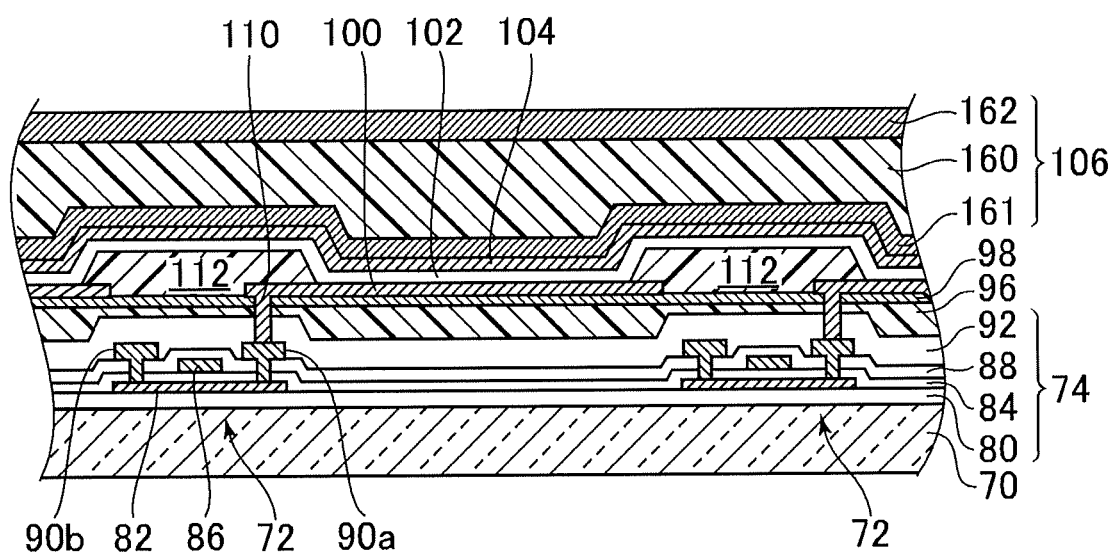
FIG. 2 is a cross sectional view of the organic EL display device illustrated in FIG. 1 along the line II-II.

FIG. 2 is a cross sectional view of the organic EL display device 1 illustrated in FIG. 1 along the line II-II. Specifically, FIG. 2 is a schematic cross sectional view of the display area A of the thin film transistor substrate 10, with the counter substrate 20 omitted. The thin film transistor substrate 10 in the display area A has a circuit layer 74, a planarization film 96, a passivation film 98, OLEDs, and a sealing layer 106 sequentially stacked in this order on the base member 70, the circuit layer 74 including a TFT 72. The base member 70 may be formed, for example, using a glass substrate or a resin film.

The circuit layer 74 in the display area A includes the TFT 72 and an electric wire (not shown) or the like. The circuit layer 74 is formed to drive the OLEDs. A part of a driving unit can be formed on the base member 70 as the circuit layer 74 in an area adjacent to the display area A. The FPC and the driver IC constituting the driving unit can be connected to the electric wire of the circuit layer 74 in the external area B or the component mount area C.

Specifically, a base layer 80 formed of inorganic insulating material is disposed on the base member 70, and a semiconductor area 82 is formed on the base layer 80. The inorganic insulating material forming the base layer 80 may include, for example, silicon nitride ($SiN_y$), silicon oxide ($SiO_x$), and a complex thereof. The semiconductor area 82 makes, for example, a channel portion and source and drain portions of a top-gate TFT 72. The semiconductor area 82 is formed of, for example, polysilicon (p-Si). The semiconductor area 82 is formed, for example, by forming a semiconductor layer (a p-Si film) on the base member 70 and then patterning the semiconductor layer such that a part thereof for use in the circuit layer 74 is selectively left.

On the channel portion of the TFT 72, a gate insulating film 84, a gate electrode 86, and an interlayer insulating layer 88 are formed in this order. The interlayer insulating layer 88 covers the gate electrode 86. The gate insulating film 84 is typically formed of Tetraethyl Orthosilicate (TEOS). The gate electrode 86 is formed by, for example, patterning a metal film formed by sputtering. The interlayer insulating layer 88 is formed of, for example, the above mentioned inorganic insulating material. Impurities are doped through ion injection into the semiconductor area 82 constituting the source portion and the drain portion of the TFT 72. A source electrode 90*a* and a drain portion 90*b* to be electrically connected to the source portion and the drain portion, respectively, of the TFT 72 are formed. With the above, the TFT 72 is formed. After formation of the TFT 72, as described above, the interlayer insulating film 92 is formed covering the TFT 72. Further, the planarization film 96 and the passivation film 98 are formed on the interlayer insulating film 92.

In the display area A, OLEDs, each corresponding to each pixel, are formed on the passivation film 98. Each OLED includes a lower electrode 100, an organic material layer 102, and an upper electrode 104. Typically, an OLED is formed by sequentially forming the lower electrode 100, the organic material layer 102, and the upper electrode 104 in this order from the base member 70 side. In this embodiment, the lower electrode 100 corresponds to a positive electrode (anode) of the OLED, and the upper electrode 104 corresponds to a negative electrode (cathode).

The lower electrode 100 is formed for every pixel in the display area A. Specifically, after formation of the planarization film 96 as described above, a contact hole 110, through which the lower electrode 100 is to be connected to the TFT 72, is formed, and a conductive film (not shown), such as an indium tin oxide (ITO) film, is formed inside the contact hole 110. Then, a passivation film 98 is formed on the planarization film 96 and the conductive film so as to fully cover the base member 70. Subsequently, the passivation film 98 on the conductive film is removed, and the lower electrode 100 is formed on the conductive film by patterning. With the above, the lower electrode 100 connected to the TFT 72 is formed for every pixel. Note that each lower electrode is formed of light transmission conductive material, such as, ITO or Indium Zinc Oxide (IZO).

After formation of the lower electrode 100, a rib 112 is formed on the boundary between pixels. The lower electrode 100 remains uncovered in the effective area of a pixel, the effective area being defined by the surrounding rib 112. After formation of the rib 112, an organic material layer 102 is formed on the lower electrode 100. The organic material layer 102 includes a light emitting layer. Specifically, the organic material layer 102 includes a hole transport layer, a light emitting layer, an electron transport layer, or the like.

The upper electrode 104 is formed covering the entire organic material layer 102 in the display area A. The thus formed upper electrode 104 is commonly in contact with the organic material layers 102 of the plurality of OLEDs in the display area A. The upper electrode 104 is formed of light transmission conductive material, such as an ultra-thin alloy of Mg and Ag, ITO, or IZO.

The sealing layer 106 is formed on the upper electrode 104 so as to fully cover the display area A. The sealing layer 106 has a laminated structure including a first sealing film 161, a sealing planarization film 160, and a second sealing film 162 stacked in this order. The first sealing film 161 and the second sealing film 162 are formed of inorganic material (for example, inorganic insulating material). Specifically, the first sealing film 161 and the second sealing film 162 are formed by forming an $SiN_y$ film by chemical vapor deposition (CVD). The sealing planarization film 160 is formed of organic material (for example, resin material, such as curable resin composition).

FIG. 3 is a cross sectional view of the organic EL display device 1 illustrated in FIG. 1 along the line III-III. Specifically, FIG. 3 is a schematic cross sectional view of apart of the thin film transistor substrate 10 between the display area A and the external area B, with the counter substrate 20 and the details of the circuit layer 74 not shown. The external area B of the thin film transistor substrate 10 differs from the display area A in that, for example, the former does not include the TFT 72 and the OLEDs. Specifically, in the external area B of the thin film transistor substrate 10, the circuit layer 74, the passivation film 98, and the sealing layer 106 are formed in this order on the base member 70.

In the external area B, a dam 97 is formed on the base member 70 (the circuit layer 74) at a position spaced apart from the planarization film 96, the dam 97 surrounding the display area A. Additionally, the passivation film 98, the first sealing film 161, and the second sealing film 162 are formed so as to cover the dam 97. The passivation film 98 is formed of inorganic insulating material, such as $SiN_y$. The passivation film 98 is thinner than the sealing films 161, 162. For example, the thickness of each of the sealing films 161, 162 is about a few μm, while that of the passivation film 98 is about sub-μm. The planarization film 160 remains inside (the display area A side) the surrounding dam 97.

The dam 97 prevents the material forming the planarization film 160 from spreading to the outside, for example, when forming the planarization film 160 having a predetermined thickness (for example, about 10 μm). In the example illustrated, the dam 97 blocks the planarization film 160 from spreading. Typically, the dam 97 is formed of resin material (for example, photosensitive resin composition) into a linear shape having predetermined width and height. In one embodiment, the dam 97 is formed when forming the planarization film 96 in the display area A.

The dam 97 includes moisture detection member. For example, the dam 97 changes its color in the presence of moisture. Note here that it will take a relatively long time after formation of the passivation film 98 covering the dam 97 until formation of the sealing film 106 (the first sealing film 161). Specifically, the external area B remains uncovered while the OLEDs are being formed in the display area A. In other words, the external area B is left in a condition in which foreign bodies are readily deposited on the external area B until formation of the first sealing film 161. Additionally, after formation of the first sealing film 161, the first sealing film 161 on the dam 97 remains uncovered, that is, in a condition in which foreign bodies are readily deposited on the first sealing film 161, while the planarization film 160 is being formed. Moreover, the passivation film 98 is very thin, and highly likely has a defect. A foreign body, if any, on the dam 97 will highly likely cause a defect because the planarization film 160 is not formed on the dam 97 and the foreign body on the dam 97 is thus not fully covered. In view of the above, inclusion of the moisture detection member in the dam 97, to which moisture likely invades, enables early detection of such invasion of moisture.

In this embodiment, the dam 97 (the moisture detection member) contains a pH indicator and water-soluble material that is selected depending on the pH indicator used. Specifically, in the case where a pH indicator (for example, phenolphthalein) having a discoloration region on the alkaline side, for example, a pH indicator being colored on the alkaline side relative to the discoloration region but transparent on the acid side, is used, basic substance (for example, sodium carbonate) is used as water-soluble material. The content rate of the pH indicator and the water-soluble material is, for example, 1 wt % to 3 wt % of the material forming the dam 97. In the case where the dam 97 is formed when forming the planarization film 96, as described above, the planarization film 96 can have the composition same as that of the dam 97. Specifically, the planarization film 96 can contain the above mentioned pH indicator and water-soluble material.

Similar to the dam 97, the sealing planarization film 160 may contain moisture detection member. For example, the sealing planarization film 160 may be formed of organic material containing the above mentioned pH indicator and water-soluble material.

The circuit layer 74 in the external area B has, for example, an electric wire (not shown). The sealing layer 106 is not formed on the outside of the dam 97 and in the component mount area C, for example, to allow readily connection of various components.

An embodiment of the present invention has been described above. The present invention, however, is not limited to the above described embodiment. For example, the structure described in the above described embodiment may be replaced by a substantially identical structure, a structure producing a substantially same effect, or a structure achieving a substantially same object.

Note that a person skilled in the art can conceive various changes and modifications of the above mentioned embodiment within the scope of the present invention. It is understood that such changes and modifications are included in the scope of the present invention. For example, any addition, deletion, and change in design of structural components, addition and deletion of a process, and change in condition which a person skilled in the art desirably made in the above described embodiment are included in the scope of the present invention as long as the gist of the present invention is not impaired.

What is claimed is:

1. An organic electro-luminescent (EL) display device comprising, in the following order:
    a base member including a display area including a plurality of pixels and an external area surrounding the display area;
    a circuit layer including a TFT;
    a planarization film;
    a lower electrode;
    an organic material layer;
    an upper electrode; and
    a sealing layer including a first sealing film formed of inorganic material, a sealing planarization film formed of organic material, and a second sealing film formed of inorganic material in this order, the sealing layer covering the display area,
    wherein
    the organic material layer is held between the lower electrode and the upper electrode in the display area,
    in the external area, a dam formed of organic material is formed at a position spaced apart from the planarization film,
    the sealing planarization film contacts with the first sealing film and the second sealing film, and is positioned on a display area side relative to the dam,
    a part of the first sealing film is positioned in the external area, a part of the second sealing film is positioned in the external area, and the first sealing film and the second sealing film cover the dam,
    the dam, the first sealing film, and the second sealing film are arranged in this order from a base member side, and the first sealing film and the second sealing film contact each other at a surface of the dam located on a side of the dam opposite from the display area side,
    the dam includes a moisture detection member,
    a passivation film disposed between the planarization film and the lower electrode, wherein a part of the passivation film is positioned in the external area, and the passivation film covers the dam.

2. An organic electro-luminescent (EL) display device comprising, in the following order:
    a base member including a display area including a plurality of pixels and an external area surrounding the display area;
    a circuit layer including a TFT;
    a planarization film;
    a passivation film;
    a lower electrode;
    an organic material layer;
    an upper electrode; and
    a sealing layer including a first sealing film formed of inorganic material, a sealing planarization film formed of organic material, and a second sealing film formed of inorganic material in this order, the sealing layer covering the display area,
    wherein
    the organic material layer is held between the lower electrode and the upper electrode in the display area,
    in the external area, a dam formed of organic material is formed at a position spaced apart from the planarization film,
    a part of the passivation film is positioned in the external area, and the planarization film and the dam are divided by the passivation film,
    the sealing planarization film contacts with the first sealing film and the second sealing film, and is positioned on a display area side relative to the dam,
    a part of the first sealing film is positioned in the external area, a part of the second sealing film is positioned in the external area, and the passivation film, the first sealing film, and the second sealing film cover the dam,
    the dam, the first sealing film, and the second sealing film are arranged in this order from a base member side, and the first sealing film and the second sealing film contact each other at a surface of the dam located on a side of the dam opposite from the display area side,
    the dam includes moisture detection member.

3. The organic EL display device according to claim 2, wherein the moisture detection member changes color thereof in a presence of moisture.

4. The organic EL display device according to claim 2, wherein the moisture detection member includes a pH indicator and water-soluble material.

5. The organic EL display device according to claim 4, wherein the pH indicator is phenolphthalein and the water-soluble material is a basic substance.

6. The organic EL display device according to claim 5, wherein the basic substance contains sodium carbonate.

7. The organic EL display device according to claim 2, wherein the dam blocks the sealing planarization film from spreading.

* * * * *